United States Patent
Tanabe

(10) Patent No.: US 8,854,615 B2
(45) Date of Patent: Oct. 7, 2014

(54) INSPECTION APPARATUS AND INSPECTION METHOD

(75) Inventor: Atsushi Tanabe, Kanazawa (JP)

(73) Assignee: Japan Display Inc., Tokyo (JP)

( * ) Notice: Subject to any disclaimer, the term of this patent is extended or adjusted under 35 U.S.C. 154(b) by 486 days.

(21) Appl. No.: 13/179,767

(22) Filed: Jul. 11, 2011

(65) Prior Publication Data

US 2012/0019817 A1    Jan. 26, 2012

(30) Foreign Application Priority Data

Jul. 26, 2010    (JP) ................................ 2010-167385

(51) Int. Cl.
  *G01N 21/00*    (2006.01)
(52) U.S. Cl.
  USPC ................... 356/239.1; 356/239.7; 356/237.2
(58) Field of Classification Search
  USPC ..................... 356/237.1–241.6, 242.1–243.8, 356/426–431, 600–640
  See application file for complete search history.

(56) References Cited

U.S. PATENT DOCUMENTS

| | | | | |
|---|---|---|---|---|
| 6,052,534 | A * | 4/2000 | Goto ................................ | 396/71 |
| 7,343,038 | B2 * | 3/2008 | Tanaka et al. .................. | 382/168 |
| 7,868,291 | B2 * | 1/2011 | Davies .......................... | 250/330 |
| 8,493,558 | B2 * | 7/2013 | Asada et al. ............... | 356/237.2 |

FOREIGN PATENT DOCUMENTS

| | | |
|---|---|---|
| CN | 2470821 Y | 1/2002 |
| EP | 1 424 551 A1 | 6/2004 |
| JP | 9-218162 | 8/1997 |
| JP | 2005-181070 A | 7/2005 |
| JP | 2009-150772 A | 7/2009 |
| WO | WO 03/010525 A1 | 2/2003 |

OTHER PUBLICATIONS

Office Action issued Jul. 15, 2014, in Chinese Patent Application No. 201110242040.3 (with English-language Translation).

* cited by examiner

*Primary Examiner* — Gregory J Toatley
*Assistant Examiner* — Jarreas C Underwood
(74) *Attorney, Agent, or Firm* — Oblon, Spivak, McClelland, Maier & Neustadt, L.L.P.

(57) ABSTRACT

According to one embodiment, an inspection apparatus includes a first monochromatic body disposed behind an inspection target including a transparent member or a semi-transparent member, relative to an observation position which deviates from a normal direction of the inspection target, a light source configured to illuminate the inspection target and disposed at such a position in front of the inspection target that an image of the light source is not reflected on the inspection target which is observed at the observation position, and a second monochromatic body disposed at such a position in front of the inspection target that an image of the second monochromatic body is reflected on the inspection target which is observed at the observation position.

5 Claims, 3 Drawing Sheets

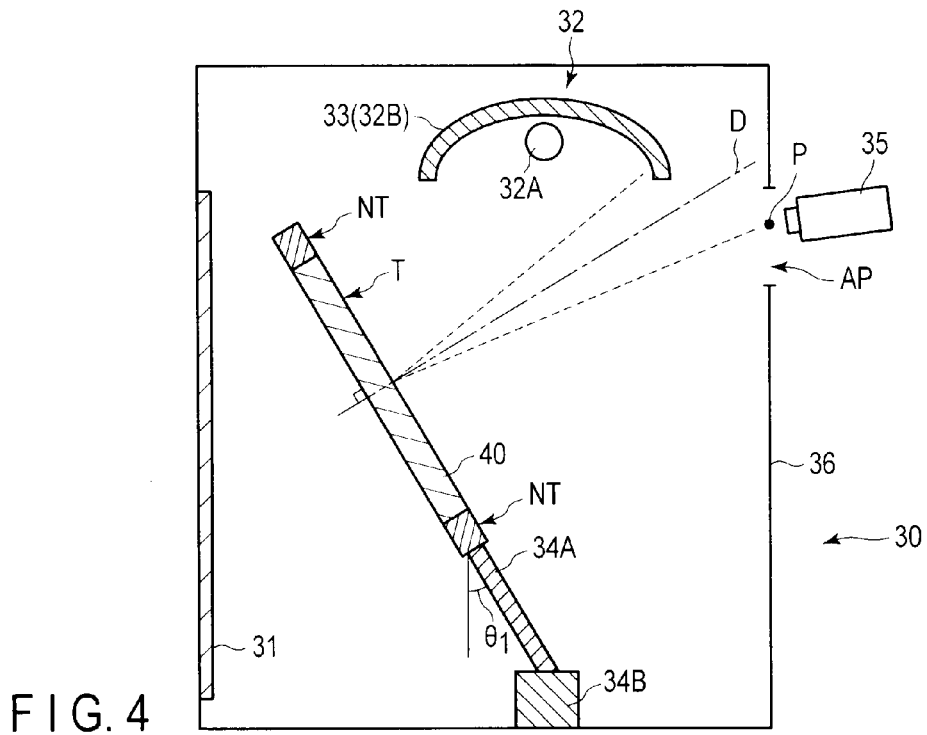
F I G. 4
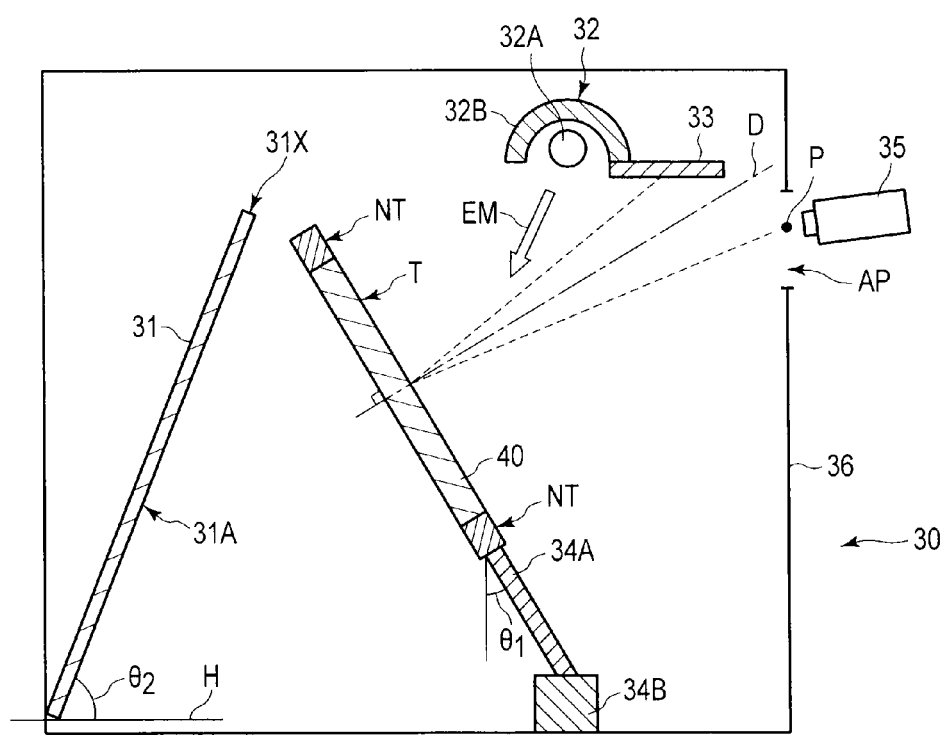
F I G. 5

INSPECTION APPARATUS AND INSPECTION METHOD

CROSS-REFERENCE TO RELATED APPLICATIONS

This application is based upon and claims the benefit of priority from prior Japanese Patent Application No. 2010-167385, filed Jul. 26, 2010, the entire contents of which are incorporated herein by reference.

FIELD

Embodiments described herein relate generally to an inspection apparatus and an inspection method.

BACKGROUND

In recent years, from the standpoint of environmental friendliness such as saving of space and power, an increasing number of commercial products have adopted liquid crystal panels or organic electroluminescence panels as display devices, as represented by liquid crystal monitors, liquid crystal TVs, mobile phones, smartphones, electronic books and notebook personal computers. In particular, in various kinds of electronic apparatuses such as smartphones, electronic books and mobile phones, transparent members or semitransparent members are used, for example, as substrates which constitute liquid crystal panels or touch panels, or as cover members of mobile phones.

If there are flaws, stains or foreign matters on the transparent member or semitransparent member, the quality of the electronic apparatus itself deteriorates. There are cases in which a thin film (including, e.g. an outer paint as a design, a logo, etc.) is patterned on the transparent member or semitransparent member. In such cases, if a defect of such a thin film fails to be inspected and the thin film is assembled in the electronic apparatus, the quality of the electronic apparatus itself would deteriorate as a matter of course, and furthermore other members would become useless in cases of repair, leading to a considerable loss of material.

There have been proposed various kinds of inspection apparatus and inspection methods for inspecting members which are applied to such electronic apparatuses.

BRIEF DESCRIPTION OF THE DRAWINGS

FIG. 4 schematically shows a second structure example of the inspection apparatus of the embodiment.

FIG. 5 schematically shows a third structure example of the inspection apparatus of the embodiment.

DETAILED DESCRIPTION

Figure 1:
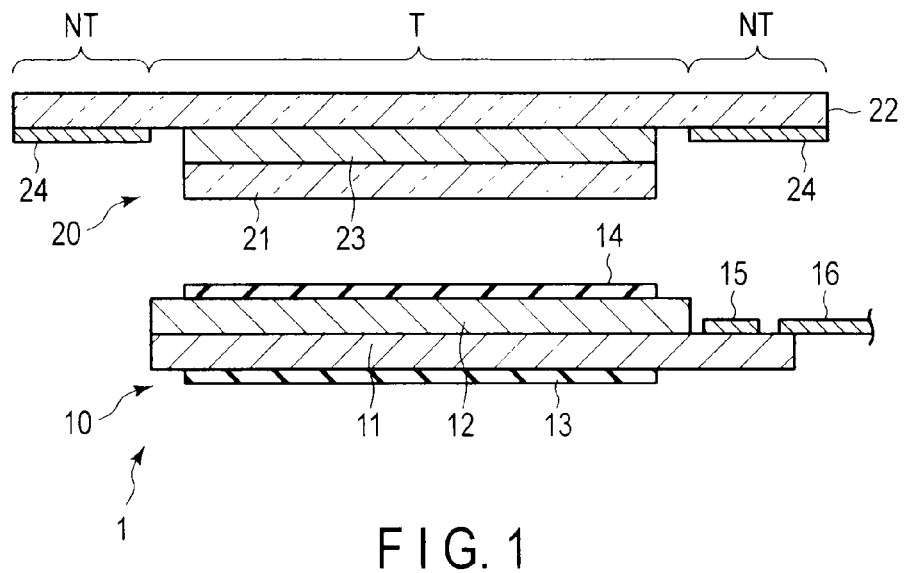
FIG. 1 is a plan view which schematically shows the structure of an electronic apparatus which includes an inspection target of an inspection apparatus and an inspection method which are described in the embodiment.

In general, according to one embodiment, an inspection apparatus comprises a first monochromatic body disposed behind an inspection target including a transparent member or a semitransparent member, relative to an observation position which deviates from a normal direction of the inspection target; a light source configured to illuminate the inspection target and disposed at such a position in front of the inspection target that an image of the light source is not reflected on the inspection target which is observed at the observation position; and a second monochromatic body disposed at such a position in front of the inspection target that an image of the second monochromatic body is reflected on the inspection target which is observed at the observation position.

According to another embodiment, an inspection apparatus comprises a first monochromatic body disposed behind an inspection target including a transparent member or a semitransparent member; a light source configured to illuminate the inspection target and disposed in front of the inspection target; and a second monochromatic body disposed in front of the inspection target, wherein an observation position, at which the inspection target is observed, is a position which deviates from a normal direction of the inspection target in front of the inspection target, is a position which deviates from a position to which the image of the light source, which is reflected on the inspection target, is regular-reflected, and is a position to which the image of the second monochromatic body, which is reflected on the inspection target, is regular-reflected.

According to another embodiment, an inspection method comprises disposing, in front of a first monochromatic body, an inspection target including a transparent member or a semitransparent member; illuminating the inspection target by a light source which is disposed in front of the inspection target; blocking light from the light source, the light traveling toward an observation position which is a position deviating from a normal direction of the inspection target, is such a position that an image of a second monochromatic body disposed in front of the inspection target is reflected on the inspection target, and is such a position that an image of the light source is not reflected on the inspection target; and inspecting the inspection target at the observation position.

The embodiment will now be described in detail with reference to the accompanying drawings. In the drawings, the structural elements having the same or similar functions are denoted by like reference numerals, and an overlapping description is omitted.

FIG. 1 is a plan view which schematically shows the structure of an electronic apparatus 1 which includes an inspection target of an inspection apparatus and an inspection method which are described in the embodiment.

Specifically, the electronic apparatus 1 includes a display panel 10. The display panel 10 is configured to include a first substrate 11, a second substrate 12 which is disposed to be opposed to the first substrate 11, and a liquid crystal layer (not shown) which is held between the first substrate 11 and second substrate 12. A first optical element 13 including, e.g. a polarizer is disposed on the outer surface of the first substrate 11. A second optical element 14 including, e.g. a polarizer is disposed on the outer surface of the second substrate 12. A driving IC chip 15 and a flexible wiring board 16 are mounted on the first substrate 11. In the meantime, the display panel 10 of the electronic apparatus 1 may be an organic electroluminescence panel.

In addition, the electronic apparatus 1 includes a cover member 20 which is disposed on a front surface of the display panel 10, which serves as a display surface or an observation surface. The cover member 20 is disposed above the second substrate 12. In the example illustrated, a space is created between the display panel 10 and the cover member 20. However, a transparent member may be interposed between the display panel 10 and the cover member 20, or the display panel 10 and the cover member 20 may be put in contact.

The cover member 20 comprises a back substrate 21, a front substrate 22, a touch panel element 23 disposed between the back substrate 21 and the front substrate 22, and a thin film 24 formed on an inner surface of the front substrate 22 (i.e. that surface of the front substrate 22, which is opposed to the display panel 10). In the meantime, there is a case in which a touch panel element 23, which is separate from the cover member 20, is added to the cover member 20, or there is a case in which a touch panel element 23, which is separate from the cover member 20, is added to the display panel 10.

In the electronic apparatus 1, the first substrate 11, second substrate 12, back substrate 21 and front substrate 22 are formed by using transparent members or semitransparent members, such as glass substrates or plastic substrates. The touch panel element 23 is formed by using a transparent member such as a transparent electrode. The thin film 24 includes a thin film which is coated as an outer decorative paint, etc., or a thin film which is printed as a logo, etc.

In the present embodiment, the inspection target corresponds to the transparent or semitransparent member itself, or a member (a finished member or a semifinished member) configured such that the structural element, such as the touch panel element 23 or thin film 24, is formed on the transparent or semitransparent member. The inspection target includes a transmissive part T and a non-transmissive part NT. For example, when the inspection target is the above-described cover member 20, the part thereof on which the non-transparent thin film 24 is formed corresponds to the non-transmissive part NT which hardly transmits light, and the part thereof on which the thin film 24 is not formed corresponds to the transmissive part T which transmits light. The transmissive part T and non-transmissive part NT reflect at least a part of ambient light at their surfaces or at interfaces between the respective structural components.

Figure 2:
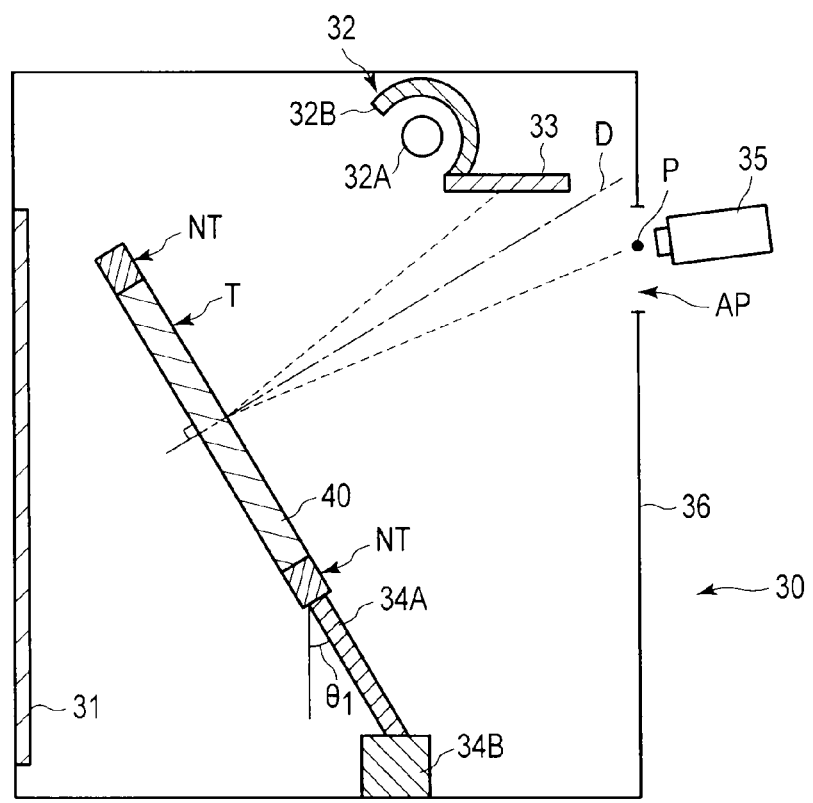
FIG. 2 schematically shows a first structure example of the inspection apparatus of the embodiment.

FIG. 2 schematically shows a first structure example of an inspection apparatus 30 of the embodiment.

Specifically, the inspection apparatus 30 is configured to include a first monochromatic body 31, a light source module 32 and a second monochromatic body 33. The inspection apparatus 30 may include a holding mechanism 34A which holds an inspection target 40. Meanwhile, instead of the holding mechanism 34A, an operator may hold the inspection target 40. In addition, the inspection apparatus 30 may include an adjusting mechanism 34B which can adjust the hold angle of the inspection target 40 by the holding mechanism 34A. Meanwhile, instead of the adjusting mechanism 34B, the operator may adjust the hold angle of the inspection target 40. In the inspection apparatus 30, an imaging device 35 may be disposed at an observation position P at which the inspection target 40 is observed. Meanwhile, instead of the imaging device 35, the operator may inspect the inspection target 40 by the naked eye at the observation position P.

In the example illustrated, the first monochromatic body 31, light source module 32, second monochromatic body 33, holding mechanism 34A and adjusting mechanism 34B are accommodated within a container 36 such as a dark chamber. An aperture AP is formed in the container 36 at a position corresponding to the observation position P. The operator performs an inspection by observing the inspection target 40 through the aperture AP from the outside of the container 36. In the case where the imaging device 35 is disposed in place of the operator, the imaging device 35 may be accommodated in the container 36 and may capture an image of the inspection target 40 from the observation position P, or may be disposed outside the container 36 and may capture an image of the inspection target 40 via the aperture AP.

The first monochromatic body 31 is disposed behind the inspection target 40, relative to the observation position P. The first monochromatic body 31 is, for instance, a sheet-like member, but it may be, for instance, a film coated on the inner surface of the container 36. The first monochromatic body 31 can be observed via the transmissive part T of the inspection target 40, when the inspection target 40 is observed from the observation position P, and can also be observed at the periphery of the inspection target 40. In short, the first monochromatic body 31 forms the background of the inspection target 40.

It is desirable to set the dimensions of the first monochromatic body 31, the distance between the first monochromatic body 31 and the inspection target 40, and the distance between the observation position P and the first monochromatic body 31, so that the first monochromatic body 31 may form the background of the entirety of the inspection target 40 when the inspection target 40 is observed from the observation position P.

In addition, it is desirable that the first monochromatic body 31 be subjected to at least one of an anti-glare (AG) process and an anti-reflection (AR) process. It is preferable that the first monochromatic body 31 be a colored body which is colored in a relatively dark color such as gray or blue, and it is more preferable that the first monochromatic body 31 be a black body.

The light source module 32 is disposed on the front side (forward side) of the inspection target 40. It is more desirable that the light source module 32 be disposed near the observation position P. The light source module 32 includes a light source 32A, and a light source cover 32B which surrounds a part of the periphery of the light source 32A.

The light source 32A is, for instance, a white fluorescent lamp, although there is no particular restriction. The light source 32A illuminates the inspection target 40. The light source 32A is disposed at such a position that the image of the light source 32A itself may not be reflected on the inspection target 40 that is observed from the observation position P. Specifically, the light source 32A is disposed at such a position that the light source 32A is observed at a position different from the observation position P when the image of the light source 32A is regular-reflected by the inspection target 40. Thus, the light source 32A is not observed at the observation position P.

In other words, the observation position P is formed at a position which deviates from the normal direction of the inspection target 40 in front of the inspection target 40. The observation position P is formed at a position deviating from a position to which the image of the light source 32A, which is reflected on the inspection target 40, is regular-reflected.

The light source cover 32B is disposed so as to block light traveling from the light source 32A toward the observation position P. Thus, the light, which is radiated from the light source 32A, does not directly strike the operator or the imaging device 35 at the observation position P. Thereby, of the light which is indirectly incident on the inspection environment (e.g. the inner surface of the container 36) or the inspection target 40, only an attenuated reflected component is radiated to the observation position P. It is possible, therefore, to prevent the image of the operator observing at the observation position P (in particular, the operator's face peering from the observation position P) or the image of the imaging device 35 disposed at the observation position P from being reflected on the inspection target 40. Moreover, the image of the light source 32A is prevented from being reflected on the inspection target 40.

The light source cover 32B is disposed at such a position that the image of the light source cover 32B itself is not reflected on the inspection target 40 that is observed at the observation position P. Specifically, the light source cover 32B is disposed at such a position that the light source cover 32B is observed at a position different from the observation position P when the image of the light source cover 32B is regular-reflected by the inspection target 40. Thus, the light source cover 32B is not observed at the observation position P. In other words, the observation position P is formed at a position deviating from a position to which the image of the light source cover 32B, which is reflected on the inspection target 40, is regular-reflected.

In the case where the surface of the light source cover 32B has a single color and the light source cover 32B is formed of a colored body (preferably, a black body) which is colored in a relatively dark color, the light source cover 32B may be disposed at such a position that the light source cover 32B is reflected on the inspection target 40.

The second monochromatic body 33 is disposed at such a position in front of the inspection target 40 that the second monochromatic body 33 is directly reflected on the inspection target 40 when the inspection target 40 is observed from the observation position P. The second monochromatic body 33 is, for instance, a sheet-like member. To be more specific, the second monochromatic body 33 is disposed at such a position that the image of the second monochromatic body 33, which is reflected on the inspection target 40, is regular-reflected to the observation position P. Thus, the second monochromatic body 33 is observed at the observation position P. In other words, the observation position P is formed at a position to which the image of the second monochromatic body 33, which is reflected on the inspection target 40, is regular-reflected.

For example, the second monochromatic body 33 is disposed near the light source cover 32B of the light source module 32. When the inspection target 40 is observed from the observation position P, the second monochromatic body 33 is reflected by the transmissive part T and non-transmissive part NT of the inspection target 40 and can be observed.

It is desirable to set the dimensions of the second monochromatic body 33, the distance between the second monochromatic body 33 and the inspection target 40, and the distance between the observation position P and the second monochromatic body 33, so that the second monochromatic body 33 may be reflected on almost the entirety of the inspection target 40 when the inspection target 40 is observed from the observation position P.

In addition, it is desirable that the second monochromatic body 33, like the first monochromatic body 31, be subjected to at least one of an anti-glare (AG) process and an anti-reflection (AR) process. In addition, it is preferable that the second monochromatic body 33, like the first monochromatic body 31, be a colored body which is colored in a relatively dark color such as gray or blue, and it is more preferable that the second monochromatic body 33 be a black body.

The holding mechanism 34A holds a peripheral edge portion of the inspection target 40 or the non-transmissive part NT of the inspection target 40, and does not lie between the transmissive part T and the first monochromatic body 31. The adjusting mechanism 34B adjusts the hold angle θ1 of the inspection target 40 which is held by the holding mechanism 34A. To be more specific, the adjusting mechanism 34B adjusts the hold angle θ1 so that the image of the second monochromatic body 33, which is reflected on the inspection target 40, is regular-reflected to the observation position P and that the image of the light source 32A, which is reflected on the inspection target 40, is regular-reflected to a position different from the observation position P (i.e. the image of the light source 32A is not regular-reflected to the observation position P). The hold angle θ1 is set such that the normal direction D of the inspection target 40 deviates from the observation position P.

The imaging device 35 captures an image of the inspection target 40 at the observation position P. The imaging device 35 is configured to include, for example, a CCD camera and a computer including software for inspecting the presence/absence of problems with the inspection target 40, based on an image captured by the CCD camera. In this case, the problems with the inspection target 40 include flaws, stains, and adhesion of foreign matter on the transparent member or semi-transparent member, and flaws, stains, adhesion of foreign matter, and pattern defects on the thin film 24.

Next, the inspection method in the above-described inspection apparatus 30 is described.

To begin with, the inspection target 40 is disposed on the front side of the first monochromatic body 31. At this time, the inspection target 40 may be held by the operator or by the holding mechanism 34A. The inspection target 40 is illuminated by the light source 32A which is disposed on the front side of the inspection target 40. At this time, the light from the light source 32A, which travels towards the observation position P which deviates from the normal direction D of the inspection target 40, is blocked by the light source cover 32B and the second monochromatic body 33. In the state in which the image of the second monochromatic body 33, which is disposed on the front side of the inspection target 40, is directly reflected on the inspection target 40 and the image of the light source 32A is not directly reflected on the inspection target 40, the inspection target 40 is observed from the observation position P and the presence/absence of problems with the inspection target 40 is inspected.

When the inspection target 40 is observed at the observation position P, the first monochromatic body 31 forms the background of the inspection target 40. Although the image of the second monochromatic body 33 is reflected on the inspection target 40, neither the image of the light source 32A nor the image of the operator or imaging device 35 at the observation position P is reflected on the inspection target 40. The operator may view the inspection target 40 in this state by the naked eye, thereby to inspect the presence/absence of problems with the inspection target 40. Alternatively, the image of the inspection target 40 in this state may be captured by the imaging device 35, and the presence/absence of problems with the inspection target 40 may be inspected based on the captured image.

When the inspection target 40 is inspected, it is desirable that the second monochromatic body 33 be reflected on almost the entirety of the inspection target 40.

Besides, in the case where the inspection target 40 is held by the holding mechanism 34A, when the inspection target 40 is inspected, it is desirable that the adjusting mechanism 34B adjust the hold angle θ1 of the inspection target 40 so that the image of the second monochromatic body 33, which is reflected on the inspection target 40, may be regular-reflected to the observation position P and that the image of the light source 32A, which is reflected on the inspection target 40, may not be regular-reflected to the observation position P. At this time, the hold angle θ1 is set such that the normal direction D of the inspection target 40 deviates from the observation position P. Thereby, neither the operator nor the imaging device 35 at the observation position P faces straight to the inspection target 40, and the image thereof is not directly reflected on the inspection target 40. Furthermore, the image of the light source 32A is not directly reflected on the inspection target 40 which is observed at the observation position P.

In the present embodiment, by the above-described inspection apparatus 30 and inspection method, transmissive observation is performed through the transmissive part T of the inspection target 40 by using the first monochromatic body 31 as the background, whereby the external appearance of the inspection target 40 is inspected. In addition, reflective observation is performed by intentionally reflecting the image of the second monochromatic body 33 on the inspection target 40, whereby the external appearance of the inspection target 40 is inspected.

At this time, in the case where the background of the inspection target 40 includes a bright area which is locally too bright, or the reflected image on the inspection target 40 includes a bright area which is locally too bright due to, for example, the direct reflection of the image of the light source 32A on the inspection target 40, the operator's attention, who is observing at the observation position P, is directed to the bright area. Besides, when the image of the inspection target 40 is captured by the imaging device 35 which is disposed at the observation position P, noise occurs in the captured image and the efficiency of the inspection may deteriorate.

Furthermore, a pattern of the background of the inspection target 40 may directly observed by transmissive observation, an undesired reflected image of, e.g. the inspection environment on the inspection target 40 may be observed by reflective observation, or the face of the operator or the imaging device 35 itself may be reflected on the inspection target 40 and may be observed by reflective observation. Thereby, the efficiency of the inspection may deteriorate.

Figure 3:
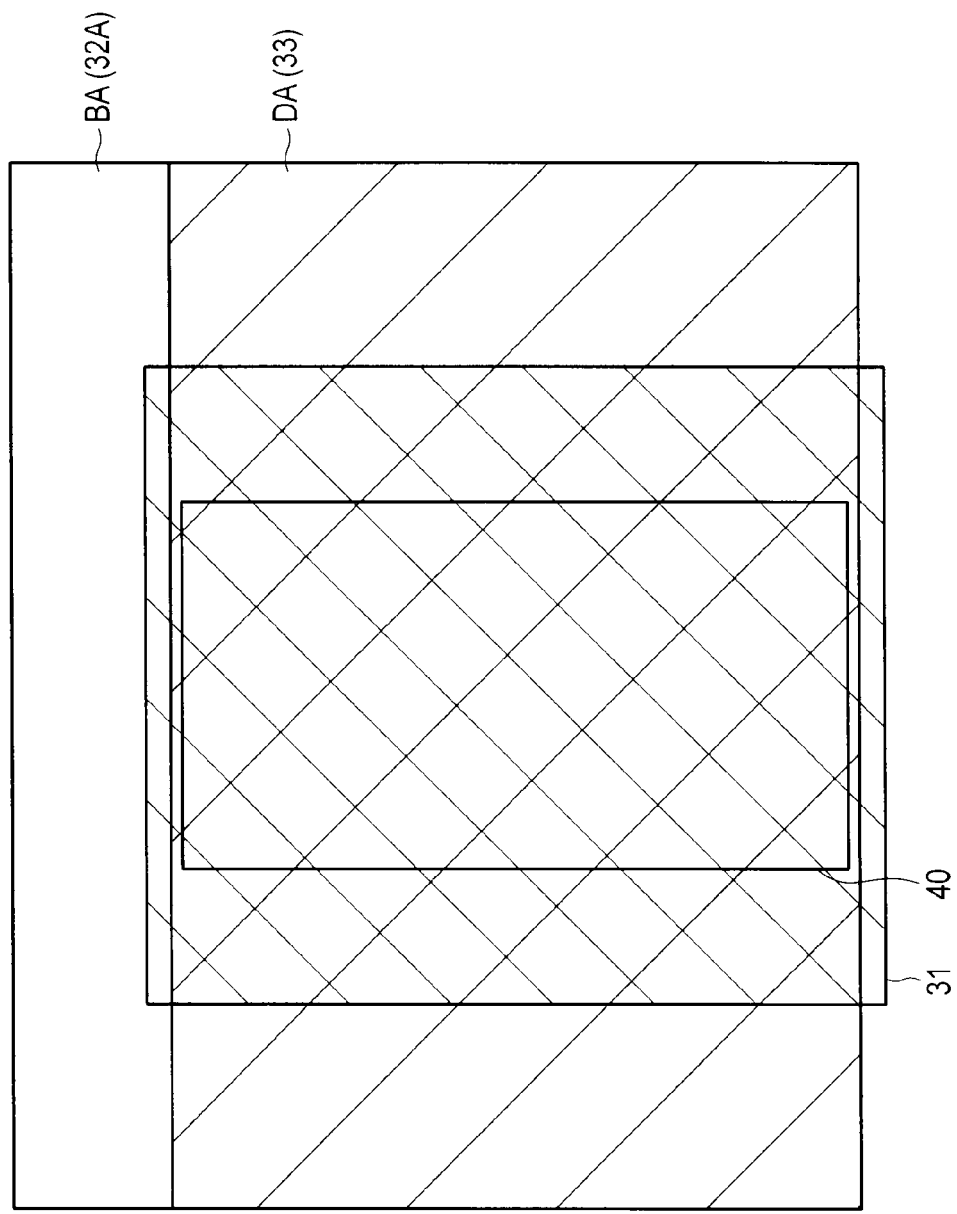
FIG. 3 is a front view which schematically shows an inspection target that is observed at an observation position of the inspection apparatus of the embodiment.

FIG. 3 is a front view which schematically shows the inspection target 40 that is observed at the observation position P of the inspection apparatus 30 of the embodiment.

According to the present embodiment, when the inspection target 40 is observed from the observation position P, the first monochromatic body 31 forms the background of the inspection target 40, and the image of the second monochromatic body 33 is reflected on the inspection target 40. The second monochromatic body 33 forms a dark area DA, and the light source 32A forms a bright area BA. In the example illustrated, the image of the second monochromatic body 33 is reflected on almost the entirety of the inspection target 40, thereby forming the dark area DA. The bright area BA is located off the inspection target 40.

Thereby, it is possible to suppress the occurrence of a local bright area on the background of the inspection target 40, or the occurrence of a local bright area due to an image reflected on the inspection target 40. In addition, a dark area can be formed on almost the entirety of the inspection target 40 by the image of the second monochromatic body 33 which is reflected on the inspection target 40. It is also possible to suppress the transmission of the pattern of the background of the inspection target 40 or the undesired reflection on the inspection target 40. In addition, since the observation position P deviates from the normal direction D of the inspection target, it is possible to solve the problem that the image of the operator or imaging device 35 itself at the observation position P is reflected. Moreover, it is possible to solve the problem that the image of the light source 32A is directly reflected on the inspection target 40 which is observed at the observation position P. Besides, the light from the light source 32A, which directly travels towards the observation position P, can be blocked by the light source cover 32B.

Therefore, in the inspection of the inspection target 40 by the operator, the visibility of the operator can be improved, the inspection load can be reduced, and the inspection work can be performed precisely and efficiently. In the inspection of the inspection target 40 by the imaging device 35, the influence of noise can be reduced, and the inspection can be performed precisely and efficiently.

In the present embodiment, in the case where the first monochromatic body 31 is subjected to at least one of the anti-glare process and anti-reflection process, the reflection and scatter of light on the surface of the first monochromatic body 31 in the inspection environment can be suppressed, and it becomes possible to suppress the undesired reflection on the inspection target 40 due to the influence of reflected light or scattered light, or the occurrence of a local bright area on the background of the inspection target 40.

In addition, in the case where the first monochromatic body 31 is a colored body which is colored in a relatively dark color, such as a black body, the reflection and scatter of light on the surface of the first monochromatic body 31 in the inspection environment can further be suppressed. Furthermore, the background of the transmissive part T of the inspection target 40 can be uniformized (i.e. a background pattern can be eliminated).

Thus, at the observation position P, the visibility can be improved when the operator performs transmissive observation of the inspection target 40. Besides, at the observation position P, the noise can be reduced when the inspection target 40 is imaged by the imaging device 35.

In the present embodiment, in the case where the second monochromatic body 33 is subjected to at least one of the anti-glare process and anti-reflection process, the undesired reflection and scatter of light due to the image of the second monochromatic body 33, which is reflected on the inspection target 40, can be suppressed, and it becomes possible to suppress the occurrence of a local bright area due to the reflection on the inspection target 40.

In addition, in the case where the second monochromatic body 33 is a colored body which is colored in a relatively dark color, such as a black body, the dark area, which is easy to inspect, can be secured, and the brightness of the image reflected on the inspection target 40 can be uniformized.

Thus, at the observation position P, the visibility can be improved when the operator performs reflective observation of the inspection target 40. Besides, at the observation position P, the noise can be reduced when the inspection target 40 is imaged by the imaging device 35. In the case where the first monochromatic body 31 and second monochromatic body 33 are films of the same color, the visibility can further be improved and the noise can further be reduced.

In the present embodiment, when the image of the second monochromatic body 33 is reflected on almost the entirety of the inspection target 40, almost the entirety of the inspection target 40 becomes a dark area which is easy to inspect, and the inspection target 40 can be inspected at the observation position P without varying the hold angle θ1 of the inspection target 40. Therefore, the efficiency of the inspection can further be improved.

Meanwhile, when the image of the second monochromatic body 33 is small, relative to the inspection target 40, and the image of the second monochromatic body 33 is reflected on a part of the inspection target 40, a part of the inspection target 40 becomes a dark area. In such a case, the inspection can be performed by gradually varying the hold angle θ1 of the inspection target 40 and shifting the position of the dark area that is formed on the inspection target 40.

In the inspection apparatus 30 of the embodiment, the inspection can be automated by the applicable use of the holding mechanism 34A, adjusting object 34B and imaging device 35.

According to the above-described inspection apparatus 30 and the inspection method using the inspection apparatus 30, since the inspection is performed within the container 36, light other than the light of the light source 32A is prevented from entering the inspection environment, or reflection and scatter of the light from the light source 32A can be suppressed. In the meantime, instead of the method using the container 36, it is possible to create a dark chamber environment for preventing reflection and scatter of light from the light source 32A, and the inspection can be performed in the dark chamber environment.

Next, other structure examples of the embodiment are described. The same structural parts as in the above-described first structure example are denoted by like reference numerals, and a detailed description thereof is omitted.

FIG. 4 schematically shows a second structure example of the inspection apparatus 30 of the embodiment.

The inspection apparatus 30 of the second structure example differs from the inspection apparatus of the first structure example shown in FIG. 2 in that the second monochromatic body 33 is the light source cover 32B which blocks light traveling from the light source 32A toward the observation position. Specifically, in the first structure example, the second monochromatic body 33 is disposed in addition to the light source cover 32B. In the second structure example, a single member serves both as the second monochromatic body 33 and the light source cover 32B.

In the second structure example, it is preferable that the second monochromatic body 33 be a colored body which is colored in a relatively dark color such as gray or blue, and it is more preferable that the second monochromatic body 33 be a black body. The second monochromatic body 33 may be a single-color film which is attached to the inner surface of the light source cover 32B, which faces the light source 32A. The second monochromatic body 33 is disposed at such a position that the image of the second monochromatic body 33, which is reflected on the inspection target 40, is regular-reflected to the observation position P.

With the second structure example, the same advantageous effects as with the first structure example can be obtained. Moreover, the number of parts, which are applied to the inspection apparatus, can be decreased.

FIG. 5 schematically shows a third structure example of the inspection apparatus 30 of the embodiment.

The inspection apparatus of the third structure example differs from the inspection apparatus of the first structure example shown in FIG. 2 in that the light from the light source 32A is made less incident on a surface 31A of the first monochromatic body 31. Specifically, the first monochromatic body 31 is disposed in such a state that an upper end 31X of the first monochromatic body 31, which is close to the light source 32A, is inclined toward the light source 32A. The first monochromatic body 31 is fixed by a fixing member (not shown). An angle θ2 between the first monochromatic body 31 and a horizontal plane H is set such that the light from the light source 32A is less easily directly radiated on the surface 31A, and the first monochromatic body 31 forms the background when the inspection target 40 is observed from the observation position P.

For example, when the directivity of the light, which is emitted from the light source 32A, is high, the angle θ2 is set such that an emission direction EM of light is substantially parallel to the surface 31A of the first monochromatic body 31. In addition, when the diffusivity of the light, which is emitted from the light source 32A, is high, the angle θ2 is set such that the emission direction EM of the light, which travels toward the first monochromatic body 31 from the light source 32A that is surrounded by the light source cover 32B and second monochromatic body 33, is substantially parallel to the surface 31A of the first monochromatic body 31.

Thereby, the reflection of, e.g. the light source 32A on the surface 31A of the first monochromatic body 31 can be suppressed, and the inspection work can be performed more precisely and efficiently.

As has been described above, according to the present embodiment, there can be provided an inspection apparatus and an inspection method which can perform an inspection with high precision and efficiency.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An inspection apparatus comprising:
   a first monochromatic body disposed behind an inspection target including a transparent member or a semitransparent member;
   a light source configured to illuminate the inspection target and disposed in front of the inspection target; and
   a second monochromatic body disposed in front of the inspection target,
   wherein an observation position, at which the inspection target is observed, is a position which deviates from a normal direction of the inspection target in front of the inspection target,
   wherein the observation position is a position which deviates from a position to which the image of the light source, which is reflected on the inspection target, is regular-reflected, and
   wherein the observation position is a position to which the image of the second monochromatic body, which is reflected on the inspection target, is regular-reflected.

2. The inspection apparatus of claim 1, wherein the second monochromatic body is a light source cover configured to block light traveling from the light source toward the observation position.

3. The inspection apparatus of claim 1, further comprising a light source cover configured to block light traveling from the light source toward the observation position.

4. The inspection apparatus of claim 1, further comprising a holding mechanism configured to hold the inspection target, and an adjusting mechanism configured to adjust a hold angle of the inspection target by the holding mechanism.

5. The inspection apparatus of claim 1, further comprising an imaging device disposed at the observation position and configured to capture an image of the inspection target.

* * * * *